United States Patent [19]

Minagawa et al.

[11] Patent Number: 4,468,223
[45] Date of Patent: Aug. 28, 1984

[54] SYRINGE

[75] Inventors: Yoshinori Minagawa; Katsuhiko Miyaguchi, both of Fujinomiya, Japan

[73] Assignee: Terumo Kabushiki Kaisha, Tokyo, Japan

[21] Appl. No.: 405,145

[22] Filed: Aug. 4, 1982

[30] Foreign Application Priority Data

Aug. 6, 1981 [JP] Japan .................. 56-123547

[51] Int. Cl.$^3$ .............................................. A61M 5/00
[52] U.S. Cl. ...................................... 604/199; 604/263
[58] Field of Search ............... 604/199, 263, 187, 192

[56] References Cited

U.S. PATENT DOCUMENTS

| 3,112,747 | 12/1963 | Cowley | 604/199 |
| 3,370,588 | 2/1968 | Burke | 604/199 |
| 3,381,813 | 5/1968 | Coanda et al. | 604/199 |
| 4,240,425 | 12/1980 | Akhaui | 604/199 |

Primary Examiner—John D. Yasko
Attorney, Agent, or Firm—Frishauf, Holtz, Goodman & Woodward

[57] ABSTRACT

A syringe comprises a cylinder with a cannula embedded in the tip portion of the cylinder and a protector cap mounted on the tip portion for protecting the cannula. Prior art syringes in which the front end of the cylinder is in close contact with the rear end of the protector are difficult to gas-sterilize because the interior space between the protector and the tip portion is sealed. The cylinder tip portion is provided with at least one first rib or channel and the cylinder front end with at least one second rib or channel that together form a passage for fluid communication between the interior of the protector cap and the outside of the cylinder such that the syringe can be fully gas-sterilized with the protector cap mounted. The second rib(s) or channel(s) also functions to restrict the advance of the protector cap to prevent damage to the cannula.

5 Claims, 12 Drawing Figures

SYRINGE

BACKGROUND OF THE INVENTION

1. Field of the Invention

This invention relates to syringes, and more particularly, to syringes having a protector cap mounted on a tip portion formed integral with a syringe cylinder.

2. Description of Prior art

Syringes often have a protector cap mounted on the tip portion of the syringe cylinder. Prior art protector caps are provided on the inner surface with projections for engaging the outer surface of the tip portion to facilitate mounting of the protector cap. The interior of the protector cap is thus sealed from the outside, escaping full sterilization when the syringe is enclosed in a package and gas-sterilized.

One common attempt to eliminate this shortcoming has been to provide the tip portion with a plurality of axially extending ribs to contact the inner surface of the protector cap. The protector cap has a step formed at a given position on the inner surface, which abuts the front ends of the ribs to stop at this position the advance of the tip portion into the protector cap during engagement of the cap. These ribs permit the interior of the protector cap to communicate with the cap exterior to allow for gas sterilization.

Since the protector cap is positioned relative to the tip portion through the abutment of the rib front ends with the protector cap inner step, the ribs and the step must be somewhat increased in width or height, resulting in an undesirable increase in the size of the protector cap. A small protector cap requires the tip portion to be of relatively small diameter, which in turn, necessitates high precision in embedding a cannula in the tip portion, resulting in a reduced yield of production. A small diameter tip portion has the associated danger that the cannula will pierce the protector wall partly because a cannula of small diameter is likely to bend and partly because such a cannula is difficult to embed perpendicularly in the tip portion. It is also difficult to firmly engage the protector cap on the tip portion because of its small size. There remains in addition the possibility that the tip portion of the cylinder may be moved beyond the step on the protector cap inner surface by any extra force to bring the protector cap rear end in sealing contact with the cylinder front end. Such sealing is undesirable for effective gas sterilization.

SUMMARY OF THE INVENTION

The present invention is arrived at through consideration of the above-mentioned drawbacks, and its primary object is to provide a syringe having a protector cap mounted on a tip portion formed integral with the front end of a cylinder wherein the interior of the protector cap communicates with the outside of the syringe such that gas sterilization can be fully effected after enclosing the syringe in a package.

A second object of the present invention is to provide a syringe of the above-mentioned type wherein the location of a cannula relative to the protector cap is controlled.

A third object of the present invention is to provide a syringe of the above-mentioned type wherein a cannula can be embedded precisely and at a minimal rejection rate and a protector cap of relatively small size be firmly fitted on the tip portion.

Yet another object of the present invention is to provide a small-sized syringe structure wherein a cannula may be firmly and precisely embedded in the tip portion and aligned with the cylinder.

The inventors have ultimately arrived at the present invention after extensive investigation of syringes to attain the above-mentioned objects.

According to the present invention, there is provided a syringe comprising a hollow cylinder, a plunger, and a protector cap, characterized in that said cylinder includes an axially outwardly extending tip portion formed contiguous and integral with the front end of said cylinder, a hollow cannula is embedded at the base in the tip portion, the interior of said cannula communicating with the interior of said cylinder, said protector cap is snugly fitted on the tip portion to sheathe said cannula and is at least partially in contact with the front end of said cylinder, and a passage is defined between said protector cap and the tip portion as well as the front end of said cylinder for the fluid communication of the interior of said protector cap with the exterior of said cylinder.

In one preferred embodiment of the present invention, the fluid passage is formed by at least one first rib or channel means on the outer surface of the tip portion and at least one second rib or channel means on the front end of the cylinder.

Preferably, the first rib means may comprise a plurality of axially extending spline-like ribs on the outer surface of the tip portion, and the second rib means may comprise a plurality of radially extending ribs on that region of the front face of the cylinder which is in contact with the protector cap.

A plurality of radially extending additional channels may be formed in that region of the front face of the cylinder which is in contact with the rear end of the protector cap.

The first ribs may be formed on the outer surface of the tip portion and the second ribs may be formed on the front face of the cylinder.

More preferably, the first and the second ribs are formed integral with each other to provide a plurality of L-shaped ribs extending across both the outer surface of the tip portion and the front face of the cylinder.

The front end of the cylinder may be circumferentially and axially extended to form an annular wall which may be formed integral with the second ribs.

The cannula is preferably bonded or cemented to the tip portion by an ultraviolet-curable adhesive.

It is to be noted that these preferred embodiments provide more specific syringe structures capable of attaining the above-mentioned and other objects in a more advantageous manner.

BRIEF DESCRIPTION OF THE DRAWINGS

The above and other objects, features and advantages of the present invention will be more fully understood by reading the following description in conjunction with the accompanying drawings, in which.

DESCRIPTION OF THE PREFERRED EMBODIMENTS

Figure 1:
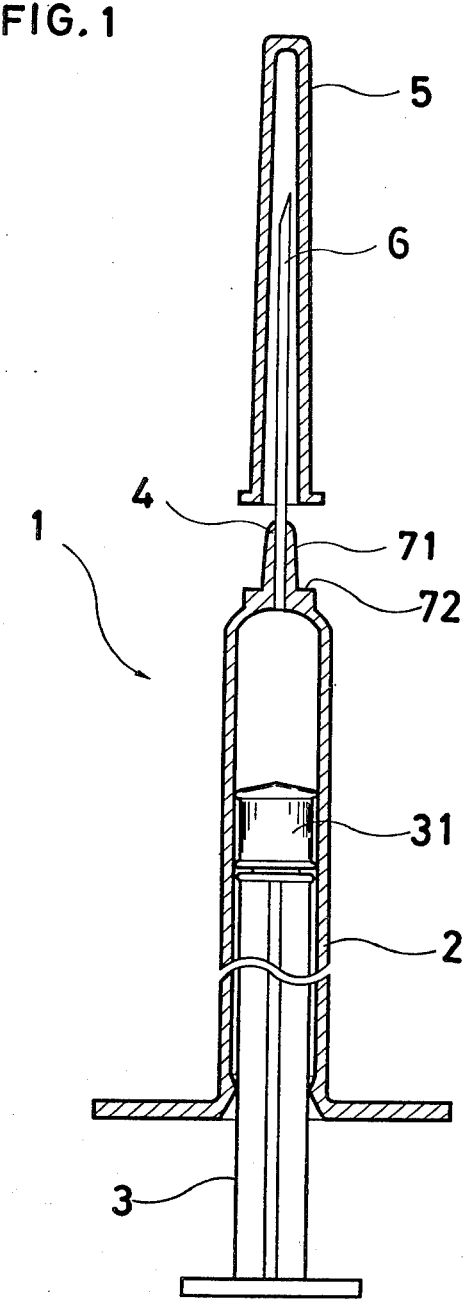
FIG. 1 is a view showing, partially in cross section, one embodiment of the syringe of the present invention with the protector cap disengaged.
Figure 2:
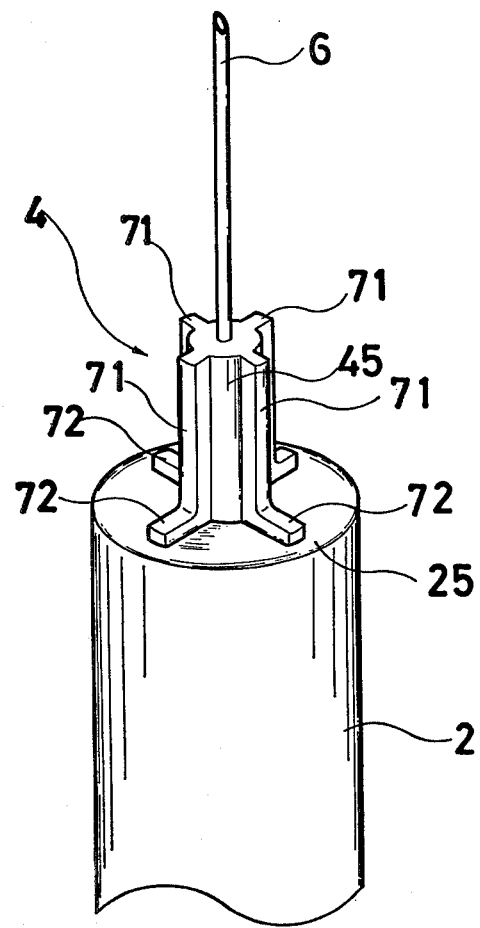
FIG. 2 is an enlarged perspective view of the tip portion of the cylinder shown in FIG. 1.

Referring to FIG. 1, a syringe according to one embodiment of the present invention is generally depicted at 1 as comprising an elongated hollow cylinder 2 in the form of a transparent tubular member made of any desired synthetic resin, for example, polypropylene, polymethylpentene, polycarbonate, polystyrene and the like. The cylinder 2 has a substantially closed front end and an open rear end. As in conventional syringes, the cylinder 2 receives a plunger 3 which is inserted through the rear opening. The plunger 3 has at its front end a gasket 31 that snugly fits in the cylinder bore such that the plunger 3 is movable in sliding contact along the inner surface of the cylinder.

The cylinder 2 is provided with an axially extending tip portion 4 which is formed contiguous and integral with the front end of the cylinder. The tip portion 4 is generally cylindrical and coaxial with the cylinder 2 and has a reduced diameter as shown in FIGS. 1 to 12. A cannula 6 at its base is axially embedded in the tip portion 4 such that the interior of the cannula communicates with the interior of the cylinder. The base of the cannula 6 is mechanically or adhesively secured to the tip portion 4. The use of the tip portion 4 formed integral with the cylinder 2 at its front end from a single piece of molding material contributes to minimized dead space left in the syringe when the plunger 3 is inserted into the cylinder 2. This feature enables the fabrication of small-volume syringes. This design together with the arrangement of the present invention not only allows syringes of a small size to be gas sterilized without requiring the high-precision fabrication of the components, but also enables reliable control of the penetration of the tip portion 4 into the protector cap.

On the tip portion 4 is snugly fitted a protector cap 5 for the purpose of protecting the cannula 6. The protector cap 5 may be of a conventional cap shape having a closed front end and an open rear end, and made of any desired synthetic resin, for example, polyethylene, polypropylene, polycarbonate, polystyrene and the like.

Figure 3:
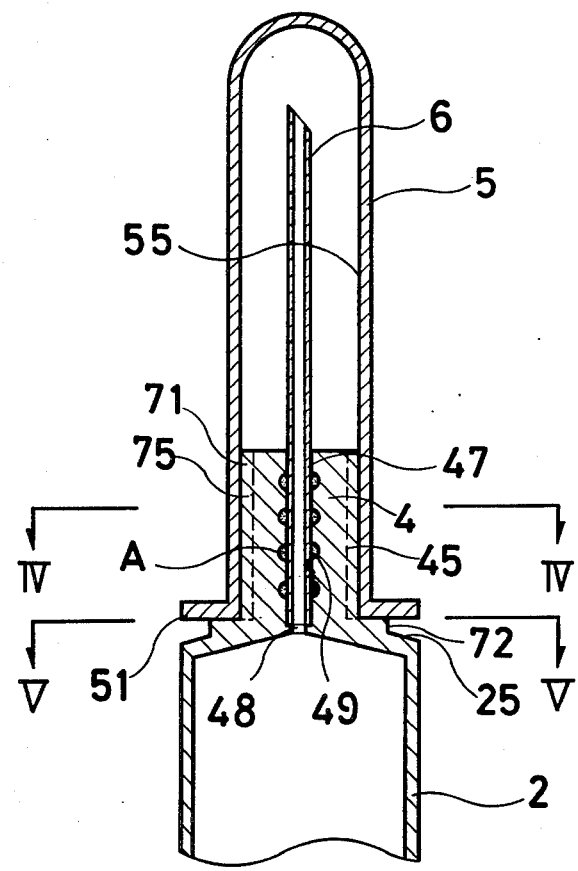
FIG. 3 is an enlarged cross-sectional view of the front portion of the syringe shown in FIG. 1, after assembly.
Figure 4:
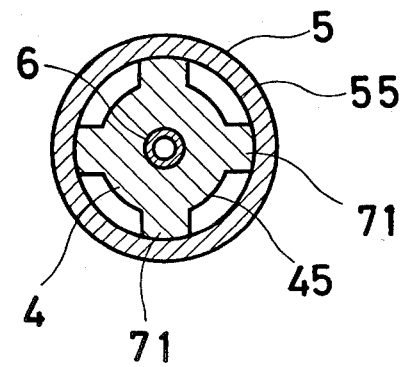
FIG. 4 and 5 are cross-sectional views of the front portion of the syringe taken along lines IV—IV and V—V in FIG. 3, respectively.
Figure 5:
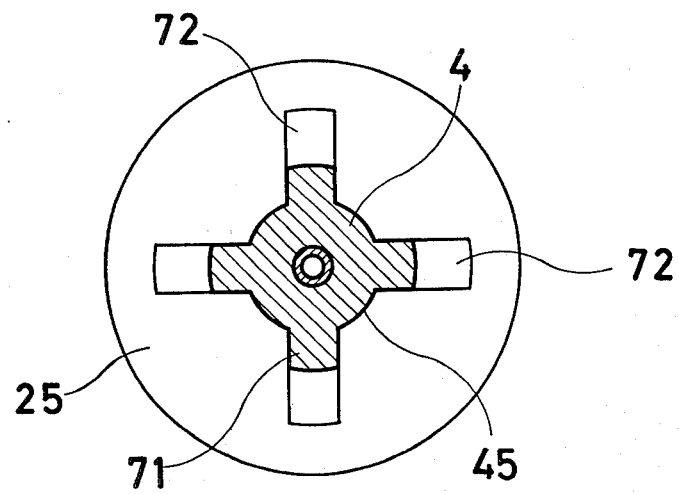

The protector cap 5 may be snugly fitted onto the tip portion 4 simply by pressing the cap against the tip portion until the cap rear end abuts the shoulder or front end of the cylinder 2 as shown in FIGS. 1 and 3.

Figure 9:
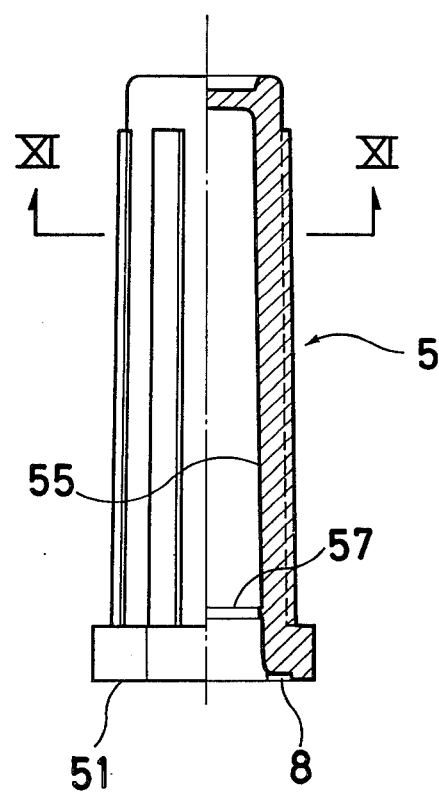
FIG. 9 is an elevation showing, partially in cross section, another example of the protector cap according to the present invention.

The protector cap 5 may have an annular ridge 57 on the inner surface 55 which may be integrally formed during manufacture of the cap as by injection molding, if desired, as shown in FIG. 9. The annular ridge 57 ensures locking engagement of the cap 5 with the tip portion 4.

In the syringe of the above-mentioned construction, according to the present invention, a passage is defined between the protector cap 5 and the tip portion 4 as well as the front end 25 of the cylinder 2 for fluid communication of the interior of the protector cap with the exterior of the cylinder 2 where the rear end of the protector cap 5 abuts at least partially the front end 25 of the cylinder 2.

The fluid communication may be achieved by a variety of structural means. Preferably, first and second rib or channel means are provided in conjunction with the tip portion 4 and the cylinder front end 25, respectively.

In one preferred embodiment, the tip portion 4 is provided on the outer surface 45 with a first rib or channel 71 which may be formed integral with the tip portion. The purpose of such a rib or channel is to prevent sealing contact between the tip portion outer surface 45 and the protector cap inner surface 55. The fluid communication means may take the form of ribs or channels as long as they carry out the required function. Generally, ribs are preferred because of their ease of fabrication.

The first rib at its outer surface bears the protector cap when the protector cap is fully engaged on the tip portion, and it at the same time defines a free space for fluid communication between the protector cap inner surface and the tip portion outer surface. The first rib is provided on that region of the outer surface of the tip portion 4 which comes in contact with the protector cap 5. To ensure the snug fit of the protector cap 5 on the tip portion 4, preferably a plurality of ribs 71 are formed on the outer surface 45 of the tip portion 4. Although the first ribs 71 are not particularly limited with respect to their number, configuration and spacing, they are preferably equally spaced. In general, three to eight first ribs 71 are used.

To provide a certain degree of close engagement of the protector cap 5 onto the tip portion 4 for a number of syringe products, the first rib means may preferably comprise a plurality of straight bar- or spline-like ribs 71 extending in the axial direction or direction of insertion of the tip portion 4 into the protector cap 5 and across the region where the tip portion is in contact with the protector cap. In this case, the engaging outer surface of the first ribs 71 may be either flat or arcuate.

The first ribs 71 are preferably formed on the outer surface 45 of the tip portion rather than the inner surface of the protector cap because of ease of fabrication. Generally, the first ribs 71 are preferably oriented on the outer surface of the tip portion in the axial direction or direction of insertion of the tip portion into the protector cap and extended over substantially the entire length of the tip portion. The axial arrangement of a plurality of first ribs enhances the snug fit of the protector cap on the tip portion. In the embodiments shown in FIGS. 1 to 8 and 12, four first ribs 71 are equally spaced and axially extended on the outer surface 45 of the tip portion 4.

Instead of the first ribs, first channels may also be provided in the outer surface of the tip portion to form a free space between the protector cap inner surface and the tip portion outer surface for fluid communication. Preferably, the first channels are located in that region of the outer surface of the tip portion 4 which comes in contact with the protector cap 5, and are axially extended over substantially the entire length of the tip portion.

In addition, the second rib or channel means is provided on the front end 25 of the cylinder 2.

The second rib means is formed integral with the front end 25 of the cylinder 2. The purpose of such ribs or channels is to prevent sealing contact between the front end 25 of the cylinder 2 and the rear end 51 of the protector cap 5. The second ribs or channels are located in a predetermined, preferably aligned, manner relative to the first ribs or channels, and cooperate with the first ribs or channels to form passages for fluid communication between the inside and outside of the protector cap so that the resultant syringe may be gas sterilized in a package. At the same time, the second rib functions as a stop member that stops the advance of the protector cap, thereby limiting the position of the cannula 6 relative to the protector cap 5 and prohibiting the cannula from accidentally piercing the protector cap.

In this case, the second rib means may preferably comprise a plurality of, generally 3 to 8 second ribs 72 spaced at equal intervals and extending radially on the front end 25 of the cylinder 2. The provision of a plurality of equally spaced second ribs 72 ensures a more precisely restricted position of the cannula 6 relative to the protector cap 5.

The second ribs 72 are preferably positioned on that region of the front end 25 of the cylinder 2 which comes in contact with the rear end 51 of the protector cap 5, as shown in FIGS. 1 to 5. As in the case of the first ribs or channels, the second ribs or channels are also not particularly limited with respect to their number, configuration and spacing, as long as they form passages for fluid communication between the inside and the outside of the protector cap.

When the second ribs 72 are provided, it is preferable from the standpoint of easy fabrication to form the first ribs 71 on the outer surface 45 of the tip portion 4 and the second ribs 72 on the front face 25 of the cylinder 2.

In forming the first and second ribs on the cylinder, it is most preferred to make these integral with each other in the form of L-shaped ribs, which results in such advantages as easier fabrication and a more secure fit of the protector cap on the tip portion. FIGS. 1 to 8 each show four L-shaped ribs 72 extending across both the cylinder front face 25 and the tip portion outer surface 45.

In a further embodiment, the protector cap 5 is provided with channels 8 in that region of the rear end 51 of the protector cap 5 which comes in contact with the front end 25 of the cylinder 2, in addition to the second ribs on the cylinder front end. These additional channels 8 form a part of the passages for the fluid communication between the inside and the outside of the protector cap.

Figure 10:
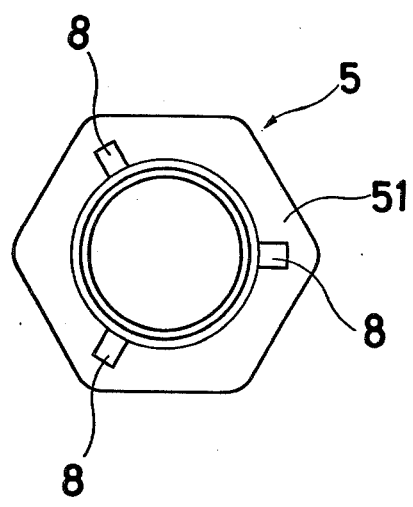
FIG. 10 is a bottom view of the protector cap of FIG. 9.
Figure 11:
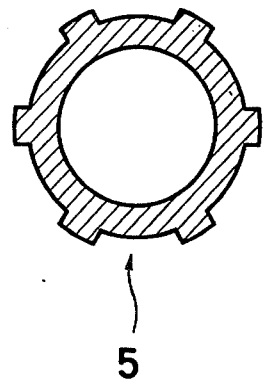
FIG. 11 is a cross-sectional view of the protector cap taken along line XI—XI in FIG. 9.

The additional channel is in the form of a notch or slot in the rear end of the protector cap. Preferably a plurality of such channels are formed. In FIGS. 9 to 11, the protector cap 5 is shown as having three channels 8 each radially extending in the rear end 51 from its radially innermost edge to a position midway across that region of the rear end which comes in contact with the front end of the cylinder 2.

Figure 6:
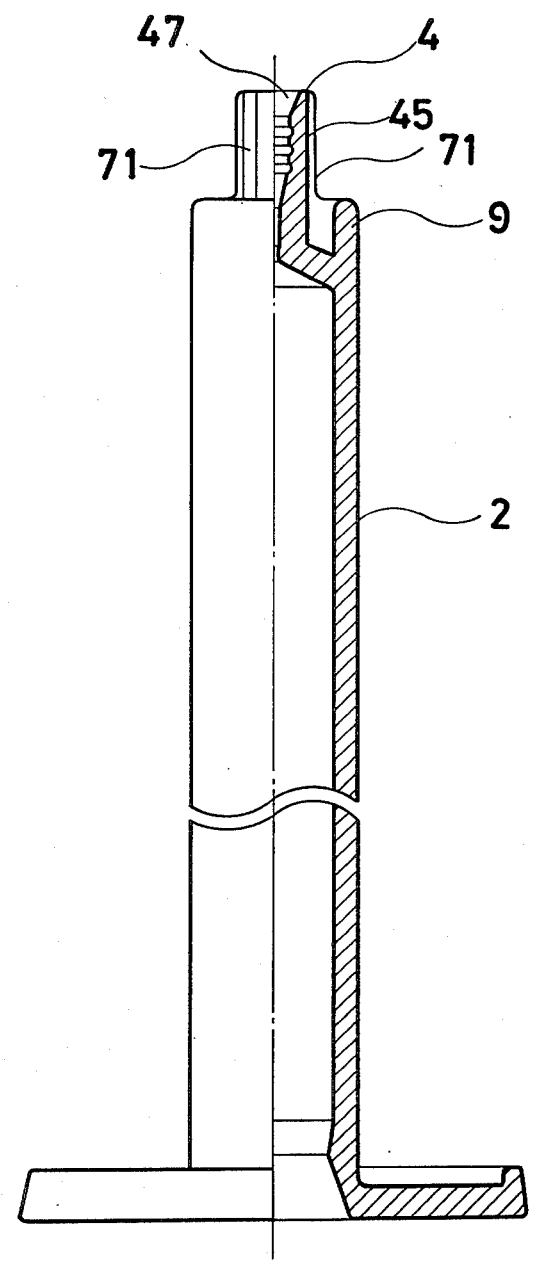
FIG. 6 is a view showing, partially in cross section, another embodiment of the syringe of the present invention.
Figure 7:
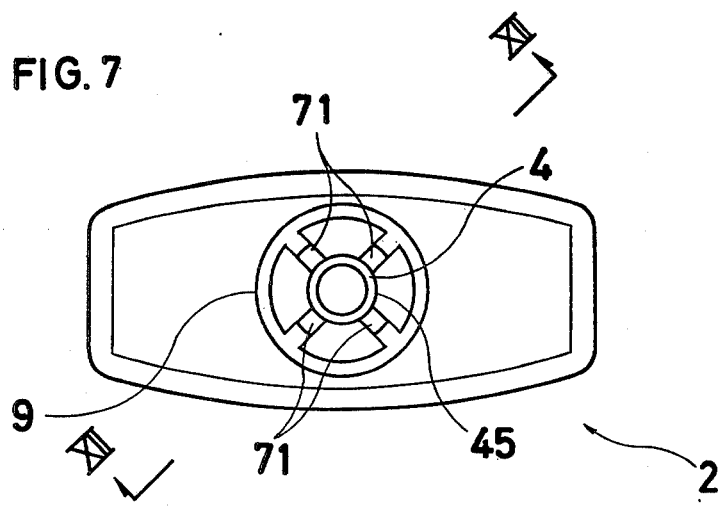
FIG. 7 is a top view of the cylinder of FIG. 6.
Figure 8:
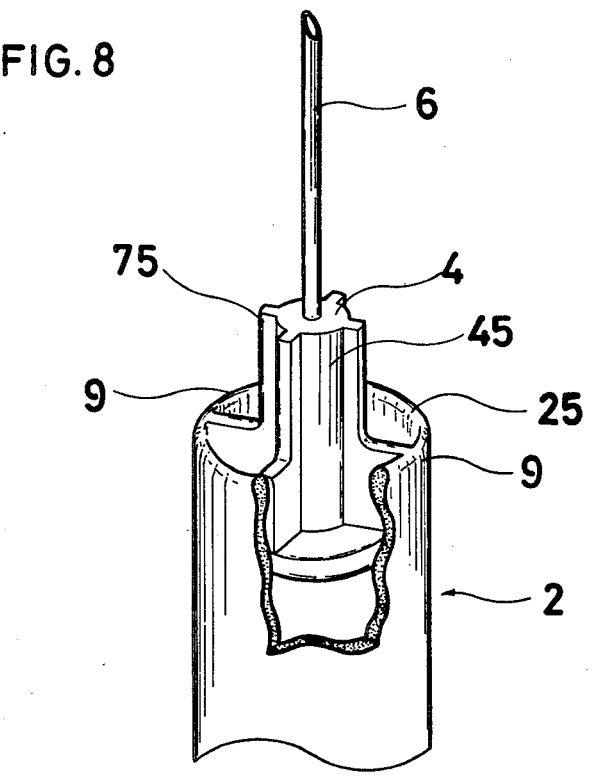
FIG. 8 is a partially cut-away perspective view of the front portion of the syringe of FIG. 6.

The cylinder 2 shown in FIGS. 6 to 8 has an annular wall 9 which extends axially and circumferentially from the outer circumference of the front end of the cylinder 2 and surrounds the tip portion 4 with a spacing. The radially extending portion of each L-shaped rib 75 (see FIG. 8) is joined to the annular wall 9. In this case, the front face of the annular wall 9 and the front edges of the radially extending portions of the ribs 75 constitute the front face 25 of the cylinder which bears the protector cap 5 at its rear face. The radially extending portions of the ribs 75 not only contact the rear face of the protector cap 5 to leave spaces for fluid communication between the interior of the protector cap and the outside of the cylinder, but also function as stops for halting the advance of the cannula into the protector cap. The protector cap 5 that is combined with such a cylinder having an annular wall integrated with L-shaped ribs has three additional channels 8 in the rear face 51 as shown in FIGS. 1 to 11 so that the passages for fluid communication are formed whenever the protector cap is engaged.

With this arrangement, the cannula is a more accurately limited position in the protector cap.

By providing the rib or channel means as described above, definite passages are formed between the protector cap 5 and the tip portion 4 as well as the front face 25 of the cylinder 2 for the fluid communication from the inside to the outside of the protector cap 5. The thus defined fluid passages permit the syringe as assembled to be enclosed in a package and gas sterilized.

It should be noted that the purpose of the tip portion 4 is to securely retain the cannula 6. Preferably, the cannula is bonded to the tip portion 4 by an ultraviolet-curable adhesive such as an oligomeric acrylate.

Figure 12:
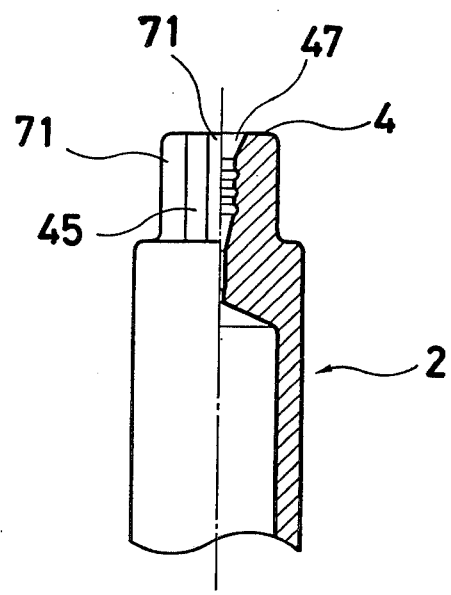
FIG. 12 is a view of the front portion of the cylinder, with the right half shown in cross section taken along line XII—XII in FIG. 7.

A preferred embodiment of the cannula 6 adhesively bonded to the tip portion 4 by a UV-curable adhesive is shown in FIGS. 3 and 12. The tip portion 4 has an axial bore 47 formed therethrough for receiving the cannula. A stop shoulder 48 is formed at the lower or inner end of the bore 47. When the cannula 6 is inserted into the bore 47, the stop shoulder 48 engages the cannula 6 at its base end to prevent the further inward movement of the cannula 6. In the inner surface of the bore 47 are formed grooves 49 which receive the adhesive to ensure an increased adhesive strength. In assembling, the cannula 6 is inserted into the bore 47 of the tip portion 4, a UV-curable adhesive A is introduced between the cannula and the bore surface, and the assembly is then exposed to ultraviolet radiation to achieve bonding.

The use of UV-curable adhesives makes the hardening step simpler than when conventional heat-curable adhesives are used because the UV-curable adhesives cannot be cured in the absence of ultraviolet radiation. It is also possible to harden only the necessary portion of the applied adhesive through local exposure and remove the remaining uncured adhesive. Few rejected syringes result from over-permeation of the adhesive, even in the case of syringes of small size. Very high adhesive strength is achieved particularly when the grooves 49 are formed in the bore 47.

EFFECTS

The syringe of the present invention, after the protector cap is press fitted on the tip portion of the cylinder, may be put in a case, envelope, container or any other type of package which is well known and commonly used in the art. The package is sealed and then subjected to gas sterilization using ethylene oxide or the like.

Gas sterilization may be effectively carried out on the entire syringe since the interior of the protector cap communicates with the outside of the cylinder through the passage defined between the protector cap and the cylinder. Such an effect is equally achievable even when the syringe is of a small size.

The position of advance of the cannula 6 and the tip portion 4 into the protector cap 5 is controlled by engaging the rear end 51 of the protector cap 5 with a part of the front end 25 of the cylinder 2 or the second ribs 72. The protector cap 5 may be put in place independent of the force used to press the cap onto the tip portion, eliminating variations in the difficulty and thoroughness of gas sterilization in different syringes. The syringes are uniform in overall length and free of the problems associated with varying overall lengths otherwise dependent upon the force used to press the cap into position.

The protector cap may be of a smaller size than in prior art syringes of the type wherein the stepped inner surface of the protector cap is engaged with the edges of the ribs on the tip portion to define a gas passage and also restricts to a given position the advance of the tip portion into the protector cap. When the protector cap is of a relatively small size, a tip portion of a relatively large diameter may be used, which facilitates the embedding of the cannula and minimizes accidental cannula penetration to improve the yield of manufacture. An additional advantage is that the protector cap is securely held on the tip portion.

When the first rib or channel means on the outer surface of the tip portion and the second rib or channel means on the front face of the cylinder form a fluid passage, all the above-mentioned advantages are obtained. In addition, the first rib or channel means and the second rib or channel means may be readily formed by conventional molding techniques such as injection molding. Even when syringes of a small size are desired, such ribs or channels may be formed without observing rigorous precision during molding. The syringes may be easily manufactured at low cost.

When a plurality of axially extending spline-like ribs are formed on the outer surface of the tip portion as the first rib means, the close fit of the protector cap on the tip portion becomes uniform among the products.

When a plurality of radially extending ribs and/or channels are formed on the region of the front face of the cylinder which comes in contact with the protector cap as the second rib and/or channel means, the mating of the tip portion and the advance of the cannula into the protector cap are controlled in a more uniform manner.

When the first ribs are formed on the outer surface of the tip portion and the second ribs are formed on the front face of the cylinder, their fabrication is facilitated.

When the first and second ribs are integrally formed to provide a plurality of L-shaped ribs extending from the tip portion outer surface to the cylinder front face, the position and snug fit of the protector cap on the tip portion are achieved in a more controlled manner and with more ease of fabrication.

The provision of an annular wall on the front end of the cylinder in combination with L-shaped ribs results in the more accurately controlled positioning of the cannula within the protector cap. When such cylinders having an annular wall combined with L-shaped ribs are molded from a plastic material, little distortion occurs in the molded cylinders upon cooling, eliminating the possibility that the tip portion is inclined with respect to the axis of the cylinder and hence, that the cannula is embedded aslant causing it to pierce the protector cap. Further, when any external force is applied to the protector cap fitted on the tip portion, the annular wall acts in concert with the tip portion to support the protector cap, preventing damage to the tip portion. An additional advantage is that the zero point of a scale may be properly marked on the outer surface of the cylinder.

The syringe of the present invention has further advantages when used in practice. When the tip portion has a length sufficient to retain the cannula, the tip portion appears short due to the presence of the annular wall. When the cannula is inserted perpendicularly into the skin, the annular wall abuts the skin to prevent the tip portion from further pressing down upon the skin, allowing the cannula to penetrate only to a predetermined depth. When the cannula is inserted at an angle, the somewhat reduced distance between the cannula tip and the annular wall allows the operator to position the cannula tip at the desired point after first bringing the annular wall into contact with the skin.

When the cannula is bonded to tip portion by an ultraviolet-curable adhesive, additional advantages are obtained including enhanced adhesive strength between the cannula and the tip portion, a minimal percentage of rejected pieces, and ease of fabrication, particularly when of syringe of small size is desired.

What we claim is:

1. A syringe comprising:
   a hollow cylinder having a front end and an axially outwardly extending tip portion formed contiguous and integral with said front end of said cylinder;
   a plunger in said cylinder;
   a plurality of integrally formed generally L-shaped ribs extending across both the outer surface of said tip portion of said cylinder and the front face of said cylinder for reinforcing said tip portion;
   said front end of said cylinder being circumferentially and axially extended to form an annular wall;
   a hollow cannula having a base which is embedded in said tip portion, the interior of said cannula communicating with the interior of said cylinder; and
   a protector cap snugly fitted on said tip portion to sheathe said cannula, said protector cap being at least partially in contact with said front end of said cylinder;
   a passage being defined between said protector cap and said tip portion and said front end of said cylinder for providing fluid communication of the interior of said protector cap with the outside of said cylinder.

2. The syringe of claim 1, wherein the portion of said hollow cannula embedded in said tip portion is bonded to said tip portion.

3. The syringe of claim 1, wherein said generally L-shaped ribs extend substantially perpendicularly from said tip portion of said cylinder.

4. The syringe of claim 1, wherein said generally L-shaped ribs have portions which extend between said tip portion of said cylinder and said annular wall of said cylinder, spaces being formed between adjacent L-shaped ribs.

5. The syringe of claim 1 wherein said cannula is bonded to said tip portion by an ultraviolet-curable adhesive.

* * * * *

UNITED STATES PATENT AND TRADEMARK OFFICE
CERTIFICATE OF CORRECTION

PATENT NO. : 4,468,223
DATED : August 28, 1984
INVENTOR(S) : Yoshinori MINAGAWA, et al It is certified that error appears in the above-identified patent and that said Letters Patent is hereby corrected as shown below:

COLUMN 6, line 17, after "the cannula" change line to read
--is stopped at a more accu---;

COLUMN 8, line 27, change "when of syringe" to --when a syringe--.

Signed and Sealed this

Twenty-third Day of April 1985

[SEAL]

Attest:

DONALD J. QUIGG

Attesting Officer

Acting Commissioner of Patents and Trademarks